United States Patent [19]

Saab

[11] Patent Number: 5,093,333
[45] Date of Patent: Mar. 3, 1992

[54] N-SUBSTITUTED-2-AMINOQUINOLINES USEFUL FOR TREATING HYPOFUNCTION OF THE CHOLINERGIC SYSTEM

[75] Inventor: Annmarie L. Saab, Pennington, N.J.

[73] Assignee: American Home Products Corporation, New York, N.Y.

[21] Appl. No.: 692,743

[22] Filed: Apr. 29, 1991

[51] Int. Cl.5 .................... A61K 31/47; A61K 31/535
[52] U.S. Cl. .................................. 514/235.2; 514/253; 514/269; 514/313; 514/314
[58] Field of Search ...................... 514/235.2, 253, 269, 514/313, 314

[56] References Cited

U.S. PATENT DOCUMENTS 4,203,988  9/1978  Bolhofer .
4,840,972  6/1989  Effland et al. ............... 514/313
4,916,135  4/1990  Effland et al. ............... 514/313

FOREIGN PATENT DOCUMENTS 42-1872  1/1967  Japan .

*Primary Examiner*—Robert W. Ramsuer
*Attorney, Agent, or Firm*—Walter Patton

[57] ABSTRACT

The compound of the formula:

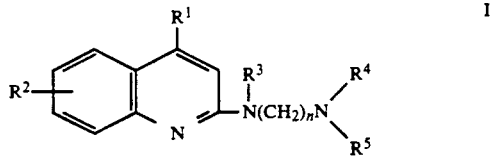

wherein
$R^1$ is H, alkyl or cycloalkyl of 1 to 6 carbon atoms;
$R^2$ is H, alkyl of 1 to 6 carbon atoms, cyano, halo, nitro, amino or mono or dialkylamino in which the alkyl groups have 1 to 6 carbon atoms;
$R^3$ is H or alkyl of 1 to 6 carbon atoms;
n is 1 to 5 and
$R^4$ and $R^5$ taken with the nitrogen atom to which they are attached are polymethylene of 4 to 6 carbon atoms, morpholino, pyrrolidin-2-on-1-yl, or a piperazin-1-yl moiety in the 4-position of which is H, alkyl of 1 to 6 carbon atoms or unsubstituted or substituted pyrimidinyl, pyridinyl, or pyrazinyl wherein the substituents are alkyl of 1 to 6 carbon atoms, alkoxyl of 1 to 6 carbon atoms, halo, cyano, nitro or trifluoromethyl and the pharmaceutically acceptable salts, hydrates and solvates thereof are $M_1$ receptor agonists useful in treatment of dementias involving the cholinergic system.

1 Claim, No Drawings

N-SUBSTITUTED-2-AMINOQUINOLINES USEFUL FOR TREATING HYPOFUNCTION OF THE CHOLINERGIC SYSTEM

BACKGROUND OF THE INVENTION

Although some forms of dementia can be treated (i.e., dementias resulting from cardiovascular disease, chemical toxins, depression, or head trauma) no effective therapy currently exists for the major form of dementia, senile dementia of the Alzheimer's type (SDAT), which accounts for more than half of all dementias, Moos et al., Med. Res. Reviews 8 (3), 353 (1988). The reason for this is that the etiology of the disease has not yet been confirmed, though many theories exist, Henderson, Acta Psychiat. Scand. 78, 257 (1988); Marx, Science 243, 1664 (1989). One theory which has gained wide acceptance is that the cognitive decline observed in patients with Alzheimer's disease and other forms of dementia is related to hypofunction of the cholinergic system, Bartus et al., Science 217, 408 (1982): Collerton, Neuroscience 19 (1), 1 (1986) and Whitehouse et al., Ann. Neurol., 10, 122 (1981). A study comparing patients with Alzheimer's disease (50), other dementias (10), and agematched controls (20) found that 50–76% of the Alzheimer's patients had a statistically significant loss of cholinergic neurons in the basal forebrain. Other studies have revealed that loss of presynaptic cholinergic neurons in the amygdala, hippocampus and neocortex related to hypofunction of the basal forebrain cholinergic system is also found in Parkinson's disease, Down's syndrome, dementia pugelistica, and some other forms of dementia, Whitehouse et al., Adv. Behav. Biology 29, 85 (1985).

The neurotransmitter of the cholinergic system is acetylcholine. Receptor binding studies on brain tissue from animals (e.g. rats) and humans have identified two major types of acetylcholine (muscarinic) receptors, presynaptic receptors on nerve terminals ($M_2$) and postsynaptic receptors ($M_1$). Postmortem examination of brain tissue from Alzheimer's patients has shown that while postsynaptic $M_1$ receptors remain intact, there is a reduction in the number of presynaptic $M_2$ receptors, Marx, ibid. In fact, there is good correlation between the degree of presynaptic neuronal loss and the severity of the dementia, Marx, ibid, Collerton, ibid.

Degeneration of presynaptic cholinergic neurons results in insufficient production of acetylcholine and understimulated postsynaptic $M_1$ receptors. Memory loss in normal humans, Bartus et al., ibid and Drachman et al., Arch. Neurol. 30, 113 (1974) and animals (e.g. cat, rat, and monkey), Bartus et al., ibid and Collerton, ibid can be artificially induced with a muscarinic antagonist, such as scopolamine. This deficit can be reversed by the anticholinesterase inhibitor, physostigmine, in both humans and monkeys, Marx, ibid and by the muscarinic agonist arecoline in rats. However, neither physostigmine nor arecoline have clinical efficacy due to undesirable side-effects, a short duration of action and a narrow active dose range. Other therapies examined in clinical studies include treatment of Alzheimer's patients and healthy elderly patients with the acetylcholine precursors choline and lecithin. No significant improvement was observed on any cognitive test.

Over the next 50 years it is predicted that nearly 20% (55 million) of the population in the United States will be over 65 years of age, Moos et al., ibid. Couple this with the fact that Alzheimer's disease alone afflicts between 5 and 15% of individuals over 65 years of age, Collerton, ibid and it becomes obvious that dementia is a major health problem for which there is an urgent need for effective therapy. Centrally acting compounds which have greater affinity for the $M_1$ receptor than the $M_2$ receptor as evidenced by in vitro receptor binding studies may be useful for the treatment of Alzheimer's disease and other disorders associated with cortical cholinergic hypofunction. $M_1$ receptor selective compounds are expected to have fewer undesirable side effects than those which are not $M_1$ selective since unwanted peripheral effects are usually associated with the $M_2$ receptor.

DESCRIPTION OF THE INVENTION

This invention relates to new and known N-substituted-2-aminoquinolines which have CNS activity. More particularly, these compounds are selective for central cholinergic $M_1$ receptors and are able to reverse scopolamine-induced hyperactivity and to improve scopolamine-induced amnesia in the radial arm maze in rats. Compounds having this activity may be useful for treatment of diseases involving hypofunction of the cortical cholinergic system.

Novel compounds of this invention are characterized by the general formula I

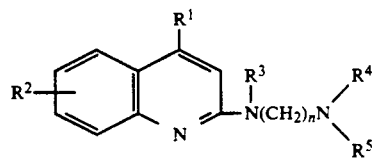

wherein $R^1$ is H, alkyl or cycloalkyl of 1 to 6 carbon atoms;

$R^2$ is H, alkyl of 1 to 6 carbon atoms, cyano, halo, nitro, amino or mono or dialkylamino in which the alkyl groups have 1 to 6 carbon atoms;

$R^3$ is H or alkyl of 1 to 6 carbon atoms;

n is 1 to 5 and $R^4$ and $R^5$ taken with the nitrogen atom to which they are attached are polymethylene of 4 to 6 carbon atoms, morpholino, pyrrolidin-2-on-1-yl, or a piperazin-1-yl moiety in the 4-position of which is H, alkyl of 1 to 6 carbon atoms or unsubstituted or substituted pyrimidinyl, pyridinyl, or pyrazinyl wherein the substituents are alkyl of 1 to 6 carbon atoms, alkoxyl of 1 to 6 carbon atoms, halo, cyano, nitro or trifluoromethyl and the pharmaceutically acceptable salts, hydrates and solvates thereof.

The known compounds of this invention are characterized by the general structure I having $R^1$, $R^2$, $R^3$, and n defined as above but $R^4$ and $R^5$ are independently H, alkyl of 1 to 6 carbon atoms, or phenyl and the pharmaceutically acceptable salts, hydrates and solvates thereof.

Of the novel compounds, from the standpoint of availability of starting compounds and production economics, the preferred compounds are those of the formula II

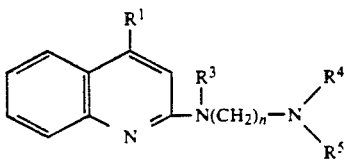

wherein
- $R^1$ is alkyl of 1 to 3 carbon atoms;
- $R^3$ is hydrogen or alkyl of 1 to 3 carbon atoms;
- n is 1 to 3 and
- $R^4$ and $R^5$ taken with the nitrogen atom to which they are attached are polymethylene of 4 to 6 carbon atoms, morpholino, pyrrolidin-2-on-1-yl, or a piperazin-1-yl moiety in which the 4-position is substituted with an alkyl group of 1 to 3carbon atoms or an unsubstituted or substituted pyrimidinyl group wherein the substituent is alkyl of 1 to 3 carbon atoms, alkoxy of 1 to 3 carbon atoms, halo, cyano, nitro or trifluoromethyl and the pharmaceutically acceptable salts, hydrates and solvates thereof.

Of the known compounds, the preferred compounds are those of the formula II wherein $R^1$, $R^2$, $R^3$, and n are as defined above for formula II but $R^4$ and $R^5$ are independently H, alkyl of 1 to 3 carbon atoms, or phenyl and the pharmaceutically acceptable salts, hydrates and solvates thereof.

The most preferred novel compounds of the present invention are designated:

4-methyl-N-[3-(4-morpholinyl)propyl]-2-quinolinamine;

N-[3-(4-morpholinyl)propyl]-2-quinolinamine;

4-methyl-N-[3-(4-methyl-1-piperazinyl)propyl]-2-quinolinamine;

4-methyl-N-[4-(4-morpholinyl)butyl]-2-quinolinamine;

4-methyl-N-[2-(4-morpholinyl)ethyl]-2-quinolinamine;

4-methyl-N-[4-(4-methyl-1-piperazinyl)butyl]-2-quinolinamine;

4-methyl-N-[3-(1-pyrrolidin-2-on)propyl]-2-quinolinamine;

4-methyl-N-[3-(1-piperidinyl)propyl]-2-quinolinamine;

4-ethyl-N-[3-(4-morpholinyl)propyl]-2-quinolinamine;

4-cyclohexyl-N-[3-(4-morpholinyl)propyl]-2-quinolinamine;

N,N-diethyl-N'-(4-methyl-2-quinolinyl)-1,3-propanediamine;

N,N-dimethyl-N'-(4-methyl-2-quinolinyl)-1,2-ethanediamine;

and the pharmaceutically acceptable salts, hydrates and solvates thereof.

The most preferred known compound of the present invention is designated: N,N-dimethyl-N'-(4-methyl-2-quinolinyl)-1,2-propanediamine and the pharmaceutically acceptable salts, hydrates and solvates thereof.

The pharmaceutically acceptable salts are those conventionally produced with organic or inorganic acids such as hydrochloric, hydrobromic, sulfuric, phosphoric, nitric, methanesulfonic, ethanesulfonic, hydroxyethanesulfonic, toluenesulfonic, naphthalenesulfonic, formic, acetic, propionic, oxalic, succinic, glycollic, lactic, malic, tartaric, citric, ascorbic, maleic, hydroxymaleic, pyruvic, phenylacetic, benzoic, paraamino benzoic, para-hydroxybenzoic, salicyclic, sulfanilic acids and the like. The term halo employed on the foregoing description of the invention is intended to embrace chlorine, bromine iodine and fluorine, the chloro or bromo groups being preferred.

Compounds of this invention may be prepared by a variety of synthetic routes using conventional methods and commercially available starting materials. Thus, for example, an unsubstituted or substituted quinoline compound containing a suitable leaving group in the 2-position such as a halogen or an S-methyl group is allowed to react with a diamino or triamino compound at elevated temperatures with or without an organic solvent. The reaction mixture may also contain an acid scavenger such as diisopropylethylamine or an inorganic salt such as ammonium chloride. The product of this reaction is an unsubstituted or substituted 2-di or triaminoquinoline of the present invention

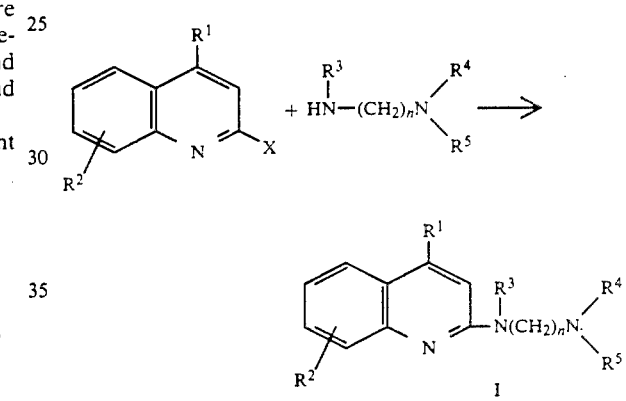

wherein $R^1, R^2, R^3, R^4, R^5$ and n are as defined above.

Compounds of this invention may also be prepared from readily available substituted or unsubstituted 4-haloquinoline compounds by allowing them to react with a Wittig reagent such as an alkyl triphenylphosphonate generated from an alkyltriphenylphosphonium halide plus a base, such as n-butyllithium in an organic solvent, such as tetrahydrofuran. The 4-alkylquinoline, thus obtained, can be converted to a 4-alkyl-2-haloquinoline by treatment with an oxidizing agent, such as m-chloroperbenzoic acid (MCPBA) in an appropriate solvent, such as chloroform, to give the corresponding 4-alkylquinoline N-oxide followed by reaction with a halogenating agent, such as phosphorus oxychloride to give a 4-alkyl-2-haloquinoline. Reaction of this 2-haloquinoline with diamines or triamines, as described above, give compounds of this invention

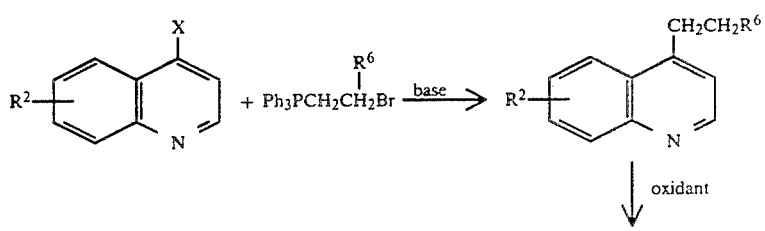

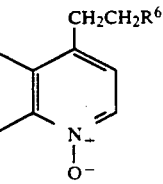
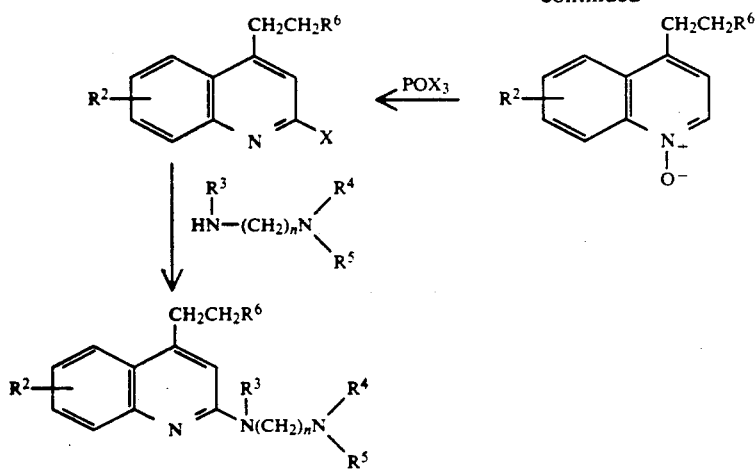

wherein $R^2, R^3, R^4, R^5$ and n are as defined above and $R^6$ is alkyl of 3 to 6 carbon atoms and X is halogen.

PRIOR ART

Japanese patent J67001872-B (1/27/67) assigned to Sankyo Co., Ltd. discloses compounds of the general formula III as active against protozoa and bacilli such as Mycobacterium tuberculosis.

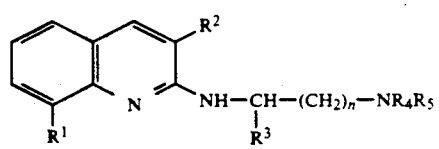

III wherein $R^1$ can be H, hydroxy or lower alkoxy, $R^2$ can be H or phenyl, $R^3$ can be H or lower alkyl, $R^4$ and $R^5$ can be the same or different lower alkyl and n can be an integer 1 to 5.

U.S. Pat. No. 3,629,418-A (April, 1972) assigned to Miles Labs Inc. discloses quinolylpiperazines of structure IV as antidepressants

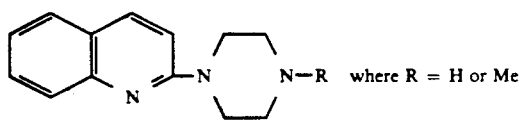

IV

U.S. Pat. No. 3,576,809-A, also assigned to Miles Labs, Inc., discloses 2-substituted-6-methoxyquinolines V as antidepressants

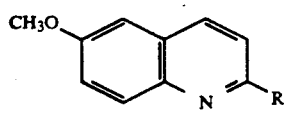

V where R = 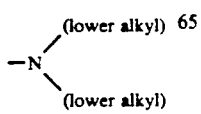

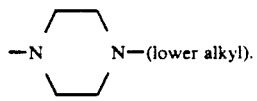

U.S. Pat. No. 4,203,988 (9/18/78) assigned to Merck & Co., Inc. discloses the synthesis of compounds of the general formula VI and their use as intermediates in the preparation of compounds of the general formula VII which are useful as inhibitors of gastric acid secretion:

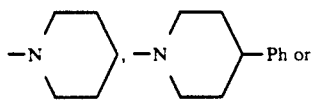

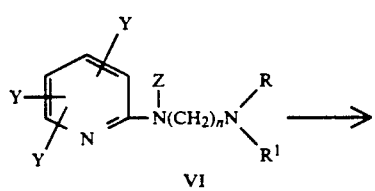

VI

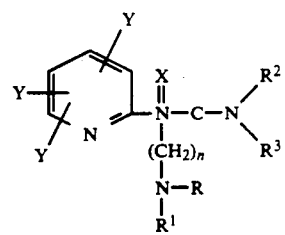

VII wherein adjacent Y-substituents on the pyridine ring may form a benzene ring and the third Y can be H or alkyl;

Z is a labile activating group or H;

X is oxygen or sulfur;

R, $R^1$, $R^2$, and $R^3$ are H, $C_1$-$C_8$ alkyl, aralkyl, $C_3$-$C_7$ cycloalkyl, $C_3$-$C_7$ cycloalkylmethyl and alkoxyalkyl, where the alkoxy and alkyl portions can separately be $C_1$-$C_4$.

The following examples of the preparation of several compound species are presented as illustrative rather than limitative elements of the invention.

EXAMPLE 1

4-Methyl-N-[3-(4-morpholinyl)propyl]-2-quinolinamine (E)-2-butenedioate 1:1 hydrate A mixture of 2-chlorolepidine (3.0 g, 17 mmol), 4,-(3-aminopropyl)morpholine (10.0 g, 68 mmol), and ammonium chloride (0.9 g, 17 mmol) was heated (oil bath, 130° C.)) with stirring under a nitrogen atmosphere until no chloro compound remained by TLC analysis (silica gel, 1:1 MeOH: EtOAc). Excess amine was removed by distillation under high vacuum and the oily residue was dissolved in $CH_2Cl_2$, washed with water (3×), dried ($MgSO_4$), and the solvent evaporated to give the free base of the title compound as a yellow oil. This was converted to the fumarate salt (fumaric acid/acetone/ether), 5.05 g (71%), m.p. 120°–125° C.

Anal. Calcd. $C_{17}H_{23}N_3O.C_4H_4O_4.H_2O$: C, 60.13; H, 6.97; N, 10.02. Found: C, 60.30; H, 6.68; N, 10.25.

EXAMPLE 2

N-[3-(4-Morpholinyl)propyl]-2-quinolinamine dihydrochloride

A mixture of 2-chloroquinoline (3.0 g, 17 mmol), 4-(3-aminopropyl)-morpholine (10.8 g, 75 mmol), and ammonium chloride (0.9 g, 17 mmol) was heated (oil bath, 130° C.)) with stirring under a nitrogen atmosphere for 24 hours. Excess amine was removed by distillation under high vacuum and the residue was purified by high pressure liquid chromatography (HPLC) to give 3.09 g (62%) of the free base of the title compound. This was converted to the dihydrochloride salt (methanol/ethereal HCl/ether) 3.37 g (56%), m.p. 250°–251° C.

Anal. Calcd. $C_{16}H_{21}N_3O.2$ HCl: C, 55.82; H, 6.73; N, 12.21. Found: C, 55.58; H, 6.73; N, 12.08.

EXAMPLE 3

4-Methyl-N-[3-(4-methyl-1-piperazinyl)propyl]-2-quinolinamine (E)-2-butenedioate (1:2) hemihydrate A mixture of 2-chlorolepidine (3.0 g, 17 mmol), 3-(4-methyl-1-piperazinyl)-propylamine (10.7 g, 68 mmol), and ammonium chloride (0.9 g, 17 mmol) was heated (oil bath, 130° C.)) with stirring under a nitrogen atmosphere for 4 days and at room temperature for 2 days Excess amine was removed by distillation under high vacuum and the residue was partitioned between $CH_2Cl_2$ and water. The organic phase was washed with water, dried, and evaporated to give 670 mg (13%) of the free base of the title compound after HPLC purification. This was converted to the difumarate salt (fumaric acid/ethanol/ether), 521 mg (6%), m.p. 110°–113° C.

Anal. Calcd. $C_{18}H_{26}N_4.2C_4H_4O_4.0.5\ H_2O$: C, 57.87; H, 6.54; N, 10.38. Found: C, 57.50; H, 6.46; N, 10.72.

EXAMPLE 4

4-Methyl-N-[4-(4-morpholinyl)butyl]-2-quinolinamine (E)-2-butenedioate (1:1.15)

A mixture of 2-chlorolepidine (3.0 g, 17 mmol), 4-(4-aminobutyl)morpholine (10.76 g, 68 mmol), and ammonium chloride (0.9 g, 17 mmol) was heated (130° C.) for 18 hours under nitrogen. Excess amine was removed by distillation under high vacuum and the residue was purified by HPLC to give 2.9 g (57%) of the free base of the title compound. This was converted to the fumarate salt (3.78 g, 94%), m.p. 145°–146° C.

Anal. Calcd. $C_{18}H_{25}N_3O.1.15C_4H_4O_4$: C, 62.70; H, 6.89; N, 9.71. Found: C, 62.61; H, 6.91; N, 9.88.

EXAMPLE 5

4-Methyl-N-[2-(4-morpholinyl)ethyl]-2-quinolinamine (E)-2-butenedioate (3:2) quarter hydrate A mixture of 2-chlorolepidine (3.0 g, 17 mmol), 4-(2-aminoethyl)morpholine (8.85 g, 68 mmol), and ammonium chloride (0.9 g, 17 mmol) was heated under reflux in a nitrogen atmosphere overnight. Excess amine was removed by distallation under high vacuum and the residue was dissolved in methylene chloride, washed with water, dried, and evaporated to give the free base of the title compound as a viscous oil. The compound was converted to the fumarate salt (5.34 g), m.p. 180°–182° C.

Anal. Calcd. $C_{16}H_{21}N_3O.0.67C_4H_4O_4.0.25\ H_2O$: C, 63.44; H, 6.89; N, 11.88. Found: C, 63.45; H, 6.62; N, 11.83.

EXAMPLE 6

4-Methyl-N-[4-(4-methyl-1-piperazinyl)butyl]-2-quinolinamine (E)-2-butenedioate (1:2) one and three quarter hydrate A mixture of 2-chlorolepidine (3.0 g, 17 mmol), 4-methyl-1-piperazinylbutylamine (11.64 g, 68 mmol), and ammonium chloride (0.9 g, 17 mmol) was heated at 130° C. in a nitrogen atmosphere for five days. Excess amine was removed by distillation under high vacuum and the residue was dissolved in methylene chloride, washed with water, dried, and evaporated to give the crude free base of the title compound as a viscous oil. Impurities were removed from the oil by HPLC on silica gel eluting with a gradient of ethyl acetate and methanol. The free base (1.25 g, 25%) was then removed by methanol containing ammonium hydroxide. The compound was dissolved in ethanol by heating, cooled and treated with three equivalents of fumaric acid in ethanol at 60° C. for 2 hours. After refrigeration overnight, the precipitate was isolated, dried, and recrystallized from ethanol to give the title compound (740 mg, 14%), mp, 290°–291° C.

Anal. Calcd. $C_{19}H_{28}N_4.2C_4H_4O_4.1.75\ H_2O$: C, 56.29; H, 6.91; N, 9.73. Found: C, 56.36; H, 6.37; N, 9.05.

EXAMPLE 7

4-Methyl-N-[3-(1-pyrrolidin-2-on)propyl]-2-quinolinamine hydrochloride three-quarter hydrate A mixture of 2-chlorolepidine (1.77 g, 10 mmol), N-(3-aminopropyl)-2-pyrrolidinone (7.11 g, 50 mmol), and ammonium chloride (0.534 g, 10 mmol) was heated at 150°–160° C. (oil bath) in a nitrogen atmosphere for three hours. Excess amine was removed by distillation under high vacuum and the residue was dissolved in methylene chloride, washed with water, dried, and evaporated to give the crude free base of the title compound as a viscous oil. The compound was purified by chromatography on silica gel eluting with 10–40% methanol in ethyl acetate to give 1.47 g (52%) as an oil. The hydrochloride salt, (1.14 g, 34%) mp 148°–149° C., was prepared by dissolving the free base in methylene chloride, treating the solution with ethereal HCl, and diluting with ether.

Anal. Calcd. $C_{17}H_{21}N_3O \cdot HCl \cdot 0.75\ H_2O$: C, 61.25; H, 7.11; N, 12.61. Found: C, 61.03; H, 7.21; N, 12.40.

EXAMPLE 8

4-Methyl-N-[3-(1-piperidinyl)propyl]-2-quinolinamine (E)-2-butenedioate (1:1) hemihydrate A mixture of 2-chlorolepidine (3.0 g, 17 mmol), 3-(1-piperidinyl)propylamine (9.7 g, 68 mmol), and ammonium chloride (0.9 g, 17 mmol) was heated at 130° C. (oil bath) in a nitrogen atmosphere for 24 hours. Excess amine was removed by distillation under high vacuum and the residue was dissolved in methylene chloride, washed with water, dried, and evaporated to give the crude free base of the title compound as a viscous oil. The crude material was purified by HPLC on silica gel eluting with mixtures of methanol, ethyl acetate, and ammonium hydroxide to give 1.31 g of pure free base which was converted to the fumarate salt 1.44 g (21%) mp, 125°-126° C.

Anal. Calcd. $C_{18}H_{25}N_3 \cdot C_4H_4O_4 \cdot 0.5\ H_2O$: C, 64.69; H, 7.40; N, 10.29. Found: C, 64.72; H, 7.24; N, 10.14.

EXAMPLE 9

4-Ethyl-N-[3-(4-morpholinyl)propyl]-2-quinolinamine dihydrochloride three quarter hydrate Ethyltriphenylphosphonium bromide (45.0 g, 0.122 m) was suspended in anhydrous dimethoxyethane under a nitrogen atmosphere and cooled to −30° C. n-Butyllithium (12.2 mL of a 1 molar solution in THF) was added and the reaction mixture was stirred at −30° to −40° C. for 1 hour. 4-Chloroquinoline (9.0 g, 0.055 m) was added and the suspension was slowly warmed to room temperature and allowed to stir overnight. After heating under reflux for 2-3 hours, 50-100 mL of solvent was distilled out and replaced by a solution of sodium carbonate (12.9 g) in water (60-80 mL). After refluxing for another 2-3 hours, the solvents were evaporated and the residue was partitioned between methylene chloride and aqueous HCl. The organic phase was extracted twice with HCl, and the combined aqueous phases were basified with sodium hydroxide (50:50) to pH 9-10, extracted with ether, dried, and evaporated to give an oil which was purified by HPLC on silica gel eluting with 1:1 ethyl acetate:hexane to give 5.54 g (64%) of 4-ethylquinoline.

m-Chloroperbenzoic acid (3.64 g of 65% pure) was stirred in chloroform and treated with anhydrous magnesium sulfate to remove water. The dried solution was filtered and added to a solution of 4-ethylquinoline in chloroform (30 mL) at 0° C. The flask was flushed with nitrogen, stoppered and placed in a freezer overnight. The chloroform solution was washed with 1M NaOH (20 mL) and then with brine, dried over magnesium sulfate and evaporated to give 2.05 g (92%) of 4-ethylquinoline N-oxide.

The N-oxide was dissolved in ice cold $POCl_3$. The solution was then heated under reflux for 30 minutes, cooled to room temperature, and carefully poured over ice with stirring. The pH of the mixture was adjusted to 6 with concentrated ammonium hydroxide (ice bath cooling). The precipitate was isolated by filtration, air dried and partitioned between ethyl acetate and water. The organic phase was separated, dried, and evaporated. The residue was purified by column chromatography on silica gel eluting with 1:9 ethyl acetate:hexane to give 1.04 (49%) of 1-chloro-4-ethylquinoline.

A mixture of 1-chloro-4-ethylquinoline (1.04 g, 5.4 mmol), 3-(1-morpholinyl)-propylamine (8.5 g, 58 mmol), and ammonium chloride (0.29 g, 5.4 mmol) was heated at 148° C. (oil bath) under a nitrogen atmosphere overnight. The reaction mixture was partitioned between methylene chloride and water. The organic phase was extracted once with water and once with brine and then dried, and evaporated to give a residue which was purified by HPLC on silica gel eluting with 3:7 methanol: ethyl acetate. The free base of the title compound (1.56 g) was then converted to the dihydrochloride salt (1.64 g, 79%) mp, 203°-208° C.

Anal. Calcd. $C_{18}H_{25}N_3O \cdot 2HCl \cdot 0.75\ H_2O$: C, 56.02; H, 7.45; N, 10.89. Found: C, 56.20; H, 7.60; N, 10.92.

EXAMPLE 10

4-Cyclohexyl-N-[3-(4-morpholinyl)propyl]-2-quinolinamine dihydrochloride one quarter hydrate A mixture of 2-chloro-4-cyclohexylquinoline (1.17 g, 4.8 mmol), 4-(3-aminopropyl)morpholine (7.0 g, 49 mmol), and ammonium chloride (0.26 g, 4.9 mmol) was heated (oil bath, 134° C.)) with stirring under a nitrogen atmosphere overnight. The reaction mixture was partitioned between methylene chloride and water. The organic phase was separated, washed once with water and once with brine, dried, and evaporated to give a residue which was purified by HPLC on silica gel eluting with 3:7 methanol:ethyl acetate to give the free base of the title compound (1.58 g) which was then converted to the dihydrochloride salt. The salt was purified by recrystallization from isopropyl alcohol to give 1.55 g (69%) mp, 145°-200° C.

Anal. Calcd. $C_{22}H_{31}N_3O \cdot 2HCl \cdot 0.7\ (CH_3)_2CHOH \cdot 0.25H_2O$: C, 61.20; H, 8.33; N, 8.88. Found: C, 61.20; H, 8.69; N, 9.01.

EXAMPLE 11

N,N-Diethyl-N'-(4-methyl-2-quinolinyl)-1,3-propanediamine dihydrochloride hemihydrate A mixture of 2-chlorolepidine (3.0 g, 17 mmol), N,N-diethyl-1,3-propanediamine (8.8 g, 68 mmol), and ammonium chloride (0.9 g, 17 mmol) was heated at 80°-100° C. with stirring under a nitrogen atmosphere overnight (23 hours). The deep yellow solution was cooled to room temperature, diluted with methylene chloride (70 mL), washed with saturated NaCl solution (3×50 mL), dried over anhydrous $Na_2SO_4$, and rotary evaporated. Excess amine was removed by distillation under high vacuum and the oily residue was purified by flash chromatography on silica gel eluting with a gradient of 100% acetonitrile to 5% ammonium hydroxide in acetonitrile. The free base of the title compound, which was obtained as a yellow oil (3.67 g, 80%), was dissolved in chloroform, treated with ethereal HCl, and diluted with ether to give the dihydrochloride salt(1.34 g, 23%) as a white solid after recrystallization from 2-PrOH and heptane, mp 201°-203° C.

Anal. Calcd. $C_{17}H_{25}N_3 \cdot 2HCl \cdot 0.5\ H_2O$: C, 57.67; H, 7.91; N, 11.82. Found: C, 57.79; H, 7.99; N, 11.89.

EXAMPLE 12

N,N-Dimethyl-N'-(4-methyl-2-quinolinyl)-1,2-ethanediamine (E)-2-butenedioate (1:1)

A mixture of 2-chlorolepidine (3.0 g, 17 mmol), N,N-dimethylethylenediamine (5.99 g, 68 mmol), and ammonium chloride (0.9 g, 17 mmol) was heated under reflux in a nitrogen atmosphere until the chloro compound was gone by TLC analysis. Excess amine was removed by distillation under high vacuum. The residue was dissolved in methylene chloride (50 mL) and washed with water (3×100 mL). Sodium bicarbonate (1 equivalent) was added to the aqueous phase which was extracted again (5×100 mL) with methylene chloride. The organic phases were combined, dried, and evaporated to give the free base of the title compound as a yellow oil (3.65 g, 94%). This was converted to the fumarate salt (4.51 g), m.p. 169°–171° C.

Anal. Calcd. $C_{14}H_{19}N_3 \cdot C_4H_4O_4$: C, 62.59; H, 6.71; N, 12.16. Found: C, 62.75; H, 6.73; N, 12.29.

EXAMPLE 13

N,N-Dimethyl-N'-(4-methyl-2-quinolinyl)-1,3-propanediamine (E)-2-butenedioate (1:2)

A mixture of 2-chlorolepidine (3.0 g, 17 mmol), N,N-dimethyl-1,3-propanediamine (6.95 g, 68 mmol), and ammonium chloride (0.9 g, 17 mmol) was heated under reflux in a nitrogen atmosphere overnight. Excess amine was removed by distillation under high vacuum and the residue was dissolved in methylene chloride, washed with water, dried, and evaporated to give the free base of the title compound as a yellow oil. The compound was converted to the fumarate salt and recrystallized from ethanol to give 2.29 g of product as a white solid, m.p. 174°–176° C.

Anal. Calcd. $C_{15}H_{21}N_3 \cdot 2C_4H_4O_4$: C, 58.09; H, 6.15; N, 8.84. Found: C, 58.40; H, 6.18; N, 9.30.

IN VITRO PHARMACOLOGY

Method for $M_1$ Receptor Binding

Compounds are tested for their ability to affect $M_1$ muscarinic binding through use of [$^3$H]-pirenzepine ([$^3$H]PZ) as a prototypic $M_1$ receptor ligand. Male Sprague-Dawley (Charles River) rats are used. Dose selection is typically in the concentration range of $10^{-9}$ to $10^{-4}$M. Test and reference compounds are dissolved and diluted in water or ethanol and are then added to the assay buffer. The appropriate vehicle is added to the assay buffer for control testing.

The rats (approximately 300 gm body weight) have free access to food and water and are housed in groups of four to six. On the test day, the rats are euthanized by decapitation and brain tissue is dissected and homogenized using a hand-held teflon-coated pestle, in 20 volumes of 0.32M sucrose (20 strokes at 4° C.). After centrifugation (747 ×g for 10 minutes at 4° C.), the resultant supernatant is decanted and recentrifuged (18677×g for 20 minutes at 4° C.) The resultant pellet is resuspended in the original volume of 0.32M sucrose and frozen. After thawing, the suspension is diluted (1:1 v/v) with 10 mM $Na_2HPO_4/KH_2PO_4$ buffer (pH=7.4). [$^3$H]PZ (0.5 nM, 0.04 μCi) is then incubated with a 100 μl sample of the tissue suspension in the above buffer (1 ml final volume, including a 10 μl sample of test compound or vehicle). One-half of the tubes also contain 2 μm atropine sulfate. After 60 minutes of incubation at 25° C. (in the dark), the binding is terminated by vacuum filtration onto Whatman GF/B filters (pre-soaked for 60 minutes in 0.1% (w/v) polyethylenimine to reduce non-specific binding). After three washes with the previously mentioned buffer (4° C., 3 ml/wash), the vacuum is allowed to run for two minutes before the filter-trapped radioactivity is assayed by liquid scintillation spectroscopy. Specific [$^3$H]PZ binding is defined as total binding minus binding in the presence of 2 μM atropine sulfate.

Presentation of Results

Data are presented as the percent inhibition ([control-test]/control×100%) or enhancement ([test-control]/control×100%) of [$^3$H]PZ binding by the test or reference compound. The $IC_{50}$ value (the drug concentration which causes a 50% inhibition of specific [$^3$H]PZ binding) is calculated through the use of the EDOSE program (with probit transformation written by Mr. Steven Nettle for use in STAT80). Increases in [$^3$H]PZ are reported as percent increase (versus control) for a given test drug concentration.

| Typical Results: | |
|---|---|
| Test Drug | $IC_{50}$ |
| Oxotremorine sesquifumarate | $1.1 \times 10^{-7}$M |
| 3-[[[(3-chlorophenyl)amino]carbonyl]oxy]-N,N,N-trimethyl-1-propynaminium chloride | $1.3 \times 10^{-6}$M |

Method for M2 Receptor Binding

In order to determine the *selectivity* of a test compound for $M_1$ versus $M_2$ receptors, the effect of test compounds on [$^3$H]-quinuclidinyl benzilate ([$^3$H]QNB) binding to $M_2$ receptors was evaluated using the same species, dose selection, and drug preparation and administration methods described above. The rats (approximately 300 gm body weight) have free access to food and water and are housed in groups of four to six. On the test day, the rats are euthanized by decapitation and the cerebellum, which contains a high proportion of $M_2$ receptors is dissected and homogenized, using a hand-held teflon-coated pestle, in 20 volumes of 0.32M sucrose (20 strokes at 4° C.). After centrifugation (747×g for 10 minutes at 4° C.), the resultant supernatant is decanted and recentrifuged (18677×g for 20 minutes at 4° C.). The resultant pellet is resuspended in the original volume of 0.32M sucrose and frozen. After thawing, the suspension is diluted (1:2 v/v) with 10 mM $Na_2HPO_4/KH_2PO_4$ buffer (pH=7.4). [$^3$H]QNB (0.23 nM, 0.01 μCi) is then incubated with a 100 μl sample of the tissue suspension in the above buffer (1 mL final volume, including a 10 μl sample of test compound or vehicle). One-half of the tubes also contain 100 μM atropine sulfate. After 60 minutes of incubation at 37° C., the binding is terminated by vacuum filtration onto Whatman GF/B filters. After three washes with previously mentioned buffer (4° C., 3 ml/wash), the vacuum is allowed to run for two minutes before the filter-trapped radioactivity is assayed by liquid scintillation spectroscopy. Specific [$^3$H]QNB binding is defined as total binding minus binding in the presence of 100 μM atropine sulfate.

Presentation of Results

Data are presented as the percent inhibition ([control-test]/control×100%) or enhancement ([test-control]/control×100%) of [$^3$H]QNB binding by the test or reference compound. The $IC_{50}$ value (the drug concentration which causes a 50% inhibition of specific [$^3$H]QNB binding) is calculated through the use of the EDOSE program (with probit transformation) written by Mr. Steven Nettler for use in STAT80. Increases in [$^3$H]QNB binding are reported as percent increases (versus control) for a given test drug concentration.

| Typical Results: | |
|---|---|
| Test Drug | $IC_{50}$ |
| Oxotremorine sesquifumarate | $1.3 \times 10^{-6}$ M |
| 3-[[[(3-chlorophenyl)amino]carbonyl]oxy]-N,N,N-trimethyl-1-propynaminium chloride | $4.2 \times 10^{-5}$ M |
| Atropine sulfate | $1.2 \times 10^{-8}$ M |

Comparison of the effects of test compounds on $M_2$ binding with effects on $M_1$ binding indicate the relative in vitro selectivity of these compounds toward $M_1$ versus $M_2$ receptors. Since the central nervous system contains a high proportion of $M_1$ receptors while muscarinic receptors in the periphery are mainly of the $M_2$ type, $M_1$ selective compounds may have therapeutic potential for the treatment of disease states in which cholinergic dysfunction is apparent, such as senile dementia of the Alzheimer's type. A summary of results for compounds of the present invention appears in Table 1.

TABLE 1

Structure:

```
       R¹
        |
     /=\
    |   |—N—(CH₂)ₙR²
     \=/   H
      |
      N
```

| EXAMPLE | n | R¹ | R² | ³H-Pirenzepine M1 IC₅₀ μM | ³H-QNB M2 IC₅₀ μM | M2/M1 |
|---|---|---|---|---|---|---|
| 1 | 3 | $CH_3$ | —N(morpholine)O | 1.2 | 69.3 | 58 |
| 2 | 3 | H | —N(morpholine)O | 2.5 | 116 | 46 |
| 3 | 3 | $CH_3$ | —N(piperazine)N.$CH_3$ | 0.6 | 28 | 46 |
| 4 | 4 | $CH_3$ | —N(morpholine)O | 0.54 | 22 | 41 |
| 5 | 2 | $CH_3$ | —N(morpholine)O | 9.7 | 200 | 21 |
| 6 | 4 | $CH_3$ | —N(piperazine)N.$CH_3$ | 0.37 | 5.5 | 15 |
| 7 | 3 | $CH_3$ | —N(pyrrolidinone)=O | 1.3 | 20 | 15 |
| 8 | 3 | $CH_3$ | —N(piperidine) | 0.42 | 4.6 | 11 |
| 9 | 3 | $C_2H_5$ | —N(morpholine)O | 2.0 | 44 | 22 |

TABLE 1-continued

[Structure: quinoline with R¹ substituent at position 4, and =N—N(H)—(CH₂)ₙR² group]

| EXAMPLE | n | R¹ | R² | ³H-Pirenzepine M1 IC$_{50}$ μM | ³H-QNB M2 IC$_{50}$ μM | M2/M1 |
|---|---|---|---|---|---|---|
| 10 | 3 | C$_6$H$_{11}$ | —N(morpholine) | 2.3 | 13 | 6 |
| 11 | 3 | CH$_3$ | —N(C$_2$H$_5$)$_2$ | 0.21 | 18 | 86 |
| 12 | 2 | CH$_3$ | —N(CH$_3$)$_2$ | 1.32 | 35 | 27 |
| 13 | 3 | CH$_3$ | —N(CH$_3$)$_2$ | 0.82 | 21 | 26 |

IN VIVO PHARMACOLOGY

Scopolamine Hyperactivity

Methods

Compounds were evaluated for the ability to attenuate scopolamine-induced hyperactivity, a proposed muscarinic M1-mediated effect. Animals were permitted to habituate for 30 minutes in locomotor activity chambers (Digiscan, Omnitech; Columbus, Ohio) in which infrared detectors were used to measure movement in 3 axes. The animals were then injected i.p. with vehicle alone, scopolamine alone (1.7 mg/kg) or both scopolamine and one dose of the test compound. Animals were then replaced in the chambers and locomotor activity was measured for an additional 1 hour period. Total activity measures (vertical+horizintal movements) were collected and statistically analyzed in four 15 minute periods.

Results 1.7 mg/kg scopolamine significantly elevated total activity at all four time points (15, 30, 45 and 60 minutes post-injection). Test compounds were considered active if there was a statistically significant reduction from the scopolamine-only control group or if there was no statistical difference from the vehicle-only or scopolamine-only control groups.

The results of experiments with the compound of Example 1 and oxotremorine are presented in Table II. The compound of Example 1 was tested at 10, 30 and 54 mg/kg i.p. The 30 and 54 mg/kg doses produced an attenuation at 30 and 45 minutes post-injection that did not differ from the scopolamine-or vehicle-only controls. Therefore, the minimum effective dose of the compound of Example 1 was considered to be 30 mg/kg. Although some effect of oxotremorine was seen at lower doses, the lack of a clear dose-response relationship led us to conclude that the minimum effective dose of oxotremorine was 0.3 mg/kg. Thus, the compound of Example 1 is considered to have in vivo M1 agonist activity which is 100-fold less effective than that of oxotremorine.

TABLE II

Effect of the compound of Example 1 and Oxotremorine on Scopolamine-Induced Hyperactivity

| Compound | N | 15 | 30 | 45 | 60 |
|---|---|---|---|---|---|
| Vehicle | 9 | 1586+ | 1107+ | 877+ | 440+ |
| Scopolamine | 9 | 4349* | 2816* | 2638* | 1858* |
| Scopolamine + Compound of Example 1: | | | | | |
| 30 mg/kg | 10 | 3792* | 2069 | 1839 | 1697* |
| 54 mg/kg | 10 | 3602* | 1899 | 1722 | 1535* |
| Vehicle | 9 | 1070+ | 1191+ | 742+ | 344+ |
| Scopolamine | 9 | 5486* | 4720* | 3718* | 3510* |
| Scopolamine + Oxotremorine: | | | | | |
| 0.03 mg/kg | 10 | 3020* | 4083 | 3332 | 2265 |
| 0.1 mg/kg | 10 | 5709* | 4305 | 3725* | 2571* |
| 0.3 mg/kg | 10 | 2523 | 1819 | 2351 | 1573 |

*P < 0.05 vs. Vehicle
+P < 0.05 vs. Scopolamine

Scopolamine-impaired Radial Arm Maze

Methods

Male Sprague-Dawley (Charles River) rats on a 23-hour food deprivation schedule were trained in an eight arm radial maze with all arms baited. Each session consisted of two maze exposures, with a time limit of 300 seconds for each exposure. After four correct choices (first exposure), each animal was removed from the maze for one hour, then returned with only the remaining four arms baited (second exposure). Choice errors, consisting of delay errors (re-entry into any of the four arms chosen during the first exposure) and current errors (re-entry into any of the four arms chosen during the second exposure), as well as total errors were recorded. Durations for each exposure were also recorded. Statistical analysis was performed using a one-way ANOVA with Dunnett's t-test comparisons. Scopolamine (0.3 mg/kg, S.C.) and the compound of Example 1 (3,10 mg/kg, I.P,.) were administrered simultaneously 30 minutes prior to the test. All compounds were solubilized in phosphate buffered saline.

Results

Scopolamine produced a significant impairment in both delay and total errors compared to the vehicle control. The 3.0 mg/kg dose of the compound of Example 1 non-significantly reduced this scoplamine impairment while the 10 mg/kg dose had no effect. The increased time measures caused by scopolamine were largely unaffected by the compound of Example 1. It is concluded that the compound of Example 1 can reduce the cognitive impairments seen after scopolamine treatment. The results are presented in Table III.

TABLE III

| | Mean Values for the Compound of Example 1 in Radial Arm Maze | | | | | | | |
|---|---|---|---|---|---|---|---|---|
| | Dose | | Mean Error | | | Mean Time (Sec.) | | |
| Treatment | mg/kg | N | Delay | Current | Total | 1,4 | 5— | Total |
| Vehicle | | 12 | 0.83 | 0 | 0.42 | 54.25 | 71.92 | 63.10 |
| Scopolamine | 0.3 | 12 | 2.80* | 1.0 | 1.90 | 87.25 | 169.80* | 128.50 |
| Scopolamine + | 3.0 | 11 | 1.77 | 0.55 | 1.14 | 90.10 | 121.73*+ | 105.91* |
| Comp. of Ex. 1 | 10.0 | 12 | 2.75 | 0.33 | 1.54* | 113.8* | 148.1* | 130.92* |

*p < 0.05 vs. vehicle
+p < 0.05 vs. scopolamine

What is claimed is:

1. The method of treating diseases involving hypofunction of the cortical cholinergic system by administering an effective amount of a compound of formula

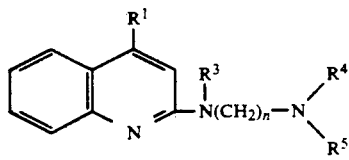

wherein $R^1$ is H, alkyl or cycloalkyl of 1 to 6 carbon atoms;
$R^2$ is H, alkyl of 1 to 6 carbon atoms, cyano, halo, nitro, amino or mono or dialkylamino in which the alkyl groups have 1 to 6 carbon atoms;
$R^3$ is H or alkyl of 1 to 6 carbon atoms;
n is 1 to 5,
$R^4$ and $R^5$ are independently H, alkyl of 1 to 6 carbon atoms, or phenyl or $R^4$ and $R^5$ taken with the nitrogen atom to which they are attached are polymethylene of 4 to 6 carbon atoms, morpholino, pyrrolidin-2-on-1-yl, or a piperazin-1-yl moiety in the 4-position of which is H, alkyl of 1 to 6 carbon atoms or unsubstituted or substituted pyrimidinyl, pyridinyl, or pyrazinyl wherein the substituents are alkyl of 1 to 6 carbon atoms, alkoxyl of 1 to 6 carbon atoms, halo, cyano, nitro or trifluoromethyl or a pharmaceutically acceptable salt, hydrate or solvate thereof.

* * * * *